United States Patent

Spry

Patent Number: 5,126,679
Date of Patent: Jun. 30, 1992

[54] SHELLED CORN MOISTURE TESTER

[76] Inventor: Robert H. Spry, 513 E. Locust, Bloomington, Ill. 61701

[21] Appl. No.: 662,701

[22] Filed: Mar. 1, 1991

[51] Int. Cl.[5] .................................. G01R 27/02
[52] U.S. Cl. ........................ 324/696; 324/692; 324/694; 324/713; 324/717; 73/73
[58] Field of Search ............... 324/692, 693, 694, 696, 324/713, 715, 717; 73/73

[56] References Cited

U.S. PATENT DOCUMENTS

| | | | |
|---|---|---|---|
| 1,987,244 | 1/1935 | Moore | 324/693 |
| 2,582,629 | 1/1952 | Hilton | 324/696 |
| 4,399,404 | 8/1983 | Resh | 324/689 |
| 4,451,781 | 5/1984 | Anderson | 324/694 |
| 4,896,795 | 1/1990 | Ediger et al. | 324/664 X |
| 4,954,783 | 9/1990 | Spry | 324/696 |

OTHER PUBLICATIONS

Kang et al., *An Electronic Probe for Estimating Ear Moisture Content of Maize*, Crop Science, vol. 18, Nov./Dec. '78, pp. 1083-1084.

Primary Examiner—Kenneth A. Wieder
Assistant Examiner—Glenn W. Brown
Attorney, Agent, or Firm—Emrich & Dithmar

[57] ABSTRACT

Apparatus for testing shelled corn in a combine storage tank during harvesting includes a plurality of charged electrodes each in the form of an elongated rod arranged in a spaced manner and positioned in a lower portion of the combine storage tank to be completely encompassed by the shelled corn. The electrodes are coupled to a moisture meter located in the combine cab allowing the operator to determine the moisture content of the corn crop at harvest. The moisture meter is easily disconnected from the electrodes and removed from the combine to permit moisture testing of corn kernels while still on the cob prior to harvest.

18 Claims, 2 Drawing Sheets

SHELLED CORN MOISTURE TESTER

BACKGROUND OF THE INVENTION

The present invention relates to electrical moisture testers for measuring the moisture content of shelled corn in a combine.

Electrical moisture testers for measuring the moisture content of vegetable matter, and in particular grains, are well known in the art. Most moisture testers operate on the principal that the electrical properties (namely, resistance or resistivity) of vegetable matter vary with the moisture content of the matter.

Some moisture testers, especially those for measuring grains, are designed to take bulk measurements after the grain or other crop has been harvested and is in storage. Such bulk measuring devices are not particularly useful or convenient in helping a farmer determine when to harvest the crop, or a seed corn company in determining "dry down" time of a new hybrid seed under development.

It is known that the relationship between cob moisture and the moisture content of corn kernels on the cob varies substantially with different corn genotypes, different moisture levels, and even with the weather. Thus, cob moisture cannot generally be correlated with corn kernel moisture. It is also known that the moisture content of the husk can influence the value of the moisture reading obtained, especially when a test is conducted in the field while the ear is still on the plant.

A moisture tester designed to estimate the moisture content of corn kernels on the cob is disclosed in an article entitled *An Electronic Probe For Estimating Ear Moisture Content of Maize* (Kang, et al, *Crop Science*, Vol. 18, Nov.-Dec. 1978, pp. 1083-1084). That device uses a pair of spaced needle-shaped conductors which are applied to penetrate the husk, kernels and cob. The moisture meter then signals the relative magnitude of the electrical resistance of the cob, kernels and husk in contact with the needle conductors.

U.S. Pat. No. 4,954,783, issued Sep. 4, 1990 in the name of the present inventor, discloses an apparatus and method for testing the moisture content of corn kernels on an ear of corn. The apparatus includes an ear cradle, a pair of electrode blades, and a circuit for measuring a moisture-dependent electrical property of the corn kernels. The major advantages of this device are that it is versatile, highly portable, reliable, accurate and inexpensive. The present invention contemplates even greater versatility and convenience for the farmer using my device.

It is important for the farmer to know the moisture content of corn at harvest. It has been estimated that the cost of drying corn is reduced by approximately 2½¢ per bushel per percentage point of moisture content down to approximately 15%. Thus, the ability to accurately measure corn moisture content allows the farmer to determine the optimum time for harvest as well as to select which of different varieties of corn to harvest depending upon moisture content. Once the farmer has made his preliminary determination to harvest a field, he has no way to assure himself that his pre-harvest tests were reliable unless, after harvesting the first few bushels, he takes a sample back to his shop for bulk testing (requiring another instrument).

OBJECTS AND SUMMARY OF THE INVENTION

Accordingly, it is an object of the present invention to provide accurate moisture testing of corn as it is harvested.

It is another object of the present invention to provide a corn moisture testing arrangement which allows for the accurate determination of kernel moisture content either on an ear of corn or after shelling in bulk form.

Yet another object of the present invention is to provide a shelled corn moisture tester for use by a commercial corn farmer which is inexpensive, easily installed in and removed from a combine, and permits the farmer to quickly and accurately determine the moisture content of the corn crop.

A further object of the present invention is to provide for the in-field testing of corn crop moisture content either in shelled bulk form or in individual kernels prior to removal from an ear of corn.

The moisture measurement of the present invention is useful, not so much because of its definitive accuracy (which can be verified or confirmed in a laboratory setting), but because of its convenience and versatility, and because it provides a reliable, repeatable, quantitative measure with sufficient accuracy that a farmer may use it in the field to measure the moisture content of corn on the cob; and he may use the same measuring instrument to connect the electrodes permanently mounted in his combine to gain a further measure of the moisture content of the shelled or bulk corn as he begins to harvest a particular field and each time he begins to fill the combine anew.

The present invention thus provides the farmer with the ability to accurately ascertain corn moisture content while the corn is in the field in order to determine the proper time for harvesting. It also permits him to use the same electronic measuring instrument to measure the moisture content of the corn in bulk form by means of a permanently mounted sensor arrangement in the combine during harvest. This is particularly important in the case of contract growers to provide a better measure of the value of a load of harvested corn.

Other features and advantages of the present invention will be apparent to persons skilled in the art from the following detailed description of a preferred embodiment accompanied by the attached drawings wherein identical reference numerals will refer to like parts in the various views.

BRIEF DESCRIPTION OF THE DRAWINGS

There is illustrated in the accompanying drawings a preferred embodiment of the corn moisture tester of the invention which, when considered in connection with the following detailed description, the invention, its construction and operation, and many of its advantages will be readily understood and appreciated.

DETAILED DESCRIPTION OF THE INVENTION

Figure 1:
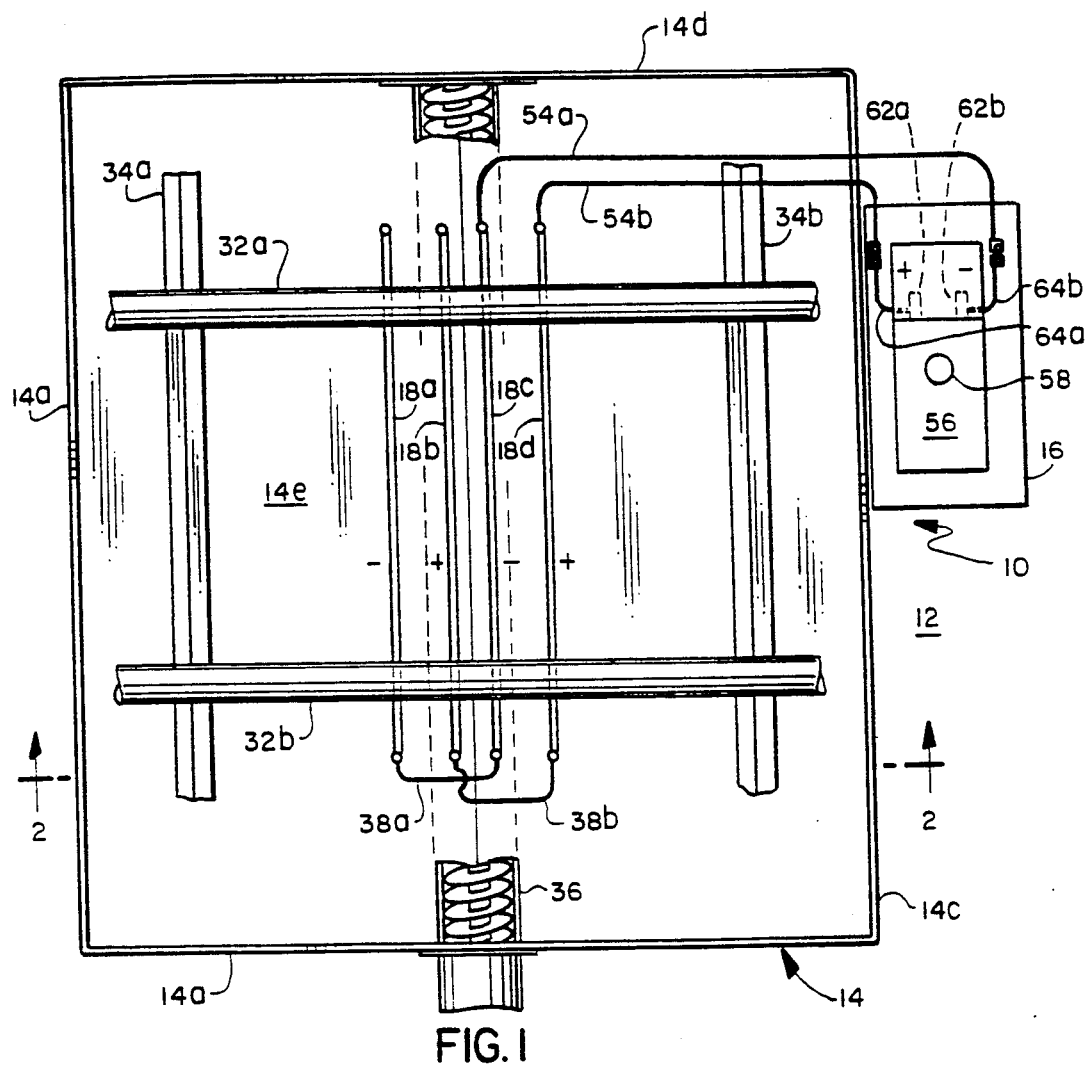
FIG. 1 is a simplified combined schematic and block diagram of a moisture tester for use with shelled corn in the storage tank of a combine in accordance with the principals of the present invention.
Figure 2:
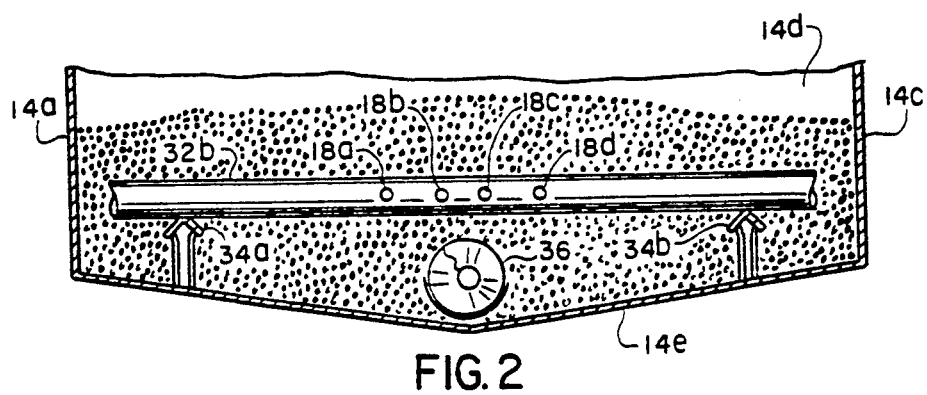
FIG. 2 is a sectional view of a portion of the shelled corn moisture tester of FIG. 1 taken along site line 2—2 therein.

Referring to FIG. 1, there is shown in simplified combined schematic and block diagram form a shelled corn moisture tester 10 for use in a combine 12 in accordance with the present invention. FIG. 2 is a sectional view of a portion of the corn moisture tester 10 shown in FIG. 1 taken along site line 2—2 therein. The combine includes a storage tank 14 and a cab 16. The combine storage tank is comprised of a plurality of side walls 14a–14d and a floor, or bottom, 14e, and is open at the top to receive corn removed from the corn husk and cob by various grain separation stages which are not shown in the figure for simplicity.

The combine cab 16, which is shown in simplified block diagram form, includes various controls manipulated by the combine operator which are also not shown for simplicity. The combine 12 itself further typically includes a forward header assembly and an aft drive and processing section which are also not shown in the figure for simplicity. The header assembly typically includes a plurality of spaced corn or row crop heads which are adapted for engaging the crops and removing the grain therefrom. The thus removed grain, in combination with crop residue such as husks in the case of corn harvesting, are then automatically delivered to the aft processing and drive portion of the combine. In addition to housing the source of propulsion, such as a diesel engine, and operator controls within the combine cab 16, the aft portion of the combine also includes a complicated threshing system for further separating the grain from the crop residue and for offloading loading the thus separated grain from the combine into a transport port vehicle such as a truck. Following separation of the grain from the crop residue, the grain is temporarily deposited in the combine storage tank 14 for subsequent off-loading. The crop residue is then exhausted from an aft portion of the combine and deposited in the field being harvested.

The shelled corn moisture tester 10 includes a plurality of spaced, elongated, rod-like electrodes 18a–18d disposed within a lower portion of the combine storage tank 14. Each of the electrodes 18a–18d is preferably comprised of an electrically conductive phosphor-bronze composition. The electrodes 18a–18d are coupled to and supported by a pair of spaced support members 32a and 32b. The support members 32a, 32b maintain the electrodes 18a–18d in fixed, spaced relation within a lower portion of the combine storage tank 14. Each of the support members 32a, 32b is preferably comprised of a non-conductive, insulating material such as polyvinyl chloride (PVC). The electrodes 18a–18d may be attached to each of the support members 32a, 32b by conventional means such as masking tape, or may be inserted through aligned apertures within each of the support members for maintaining the electrodes in spaced relation. Each of the support members 32a, 32b is, in turn, positioned upon and supported by a pair of spaced storage tank brace bars 34a and 34b. Each of the brace bars 34a, 34b is provided with a generally inverted V-shaped upper portion upon which the support members 32b and 32a rest as particularly shown in FIG. 2. The combination of the brace bars 34a, 34b and support members 32a, 32b maintains the four electrodes 18a–18d approximately one foot above the storage tank bottom 14e. Also positioned in a lower portion of the storage tank 14 is a discharge auger 36 for off-loading grain stored in the storage tank. The discharge auger 36 extends through an aperture in a wall of the storage tank 14 and is positioned generally along a centerline of the storage tank and immediately below the four electrodes 18a–18d. The electrodes 18a–18d are preferably positioned approximately 12 inches above the discharge gauge 36 in a typical installation.

As shown in FIG. 1, adjacent ends of the first and third electrodes 18a and 18c are coupled by means of an electrical lead 38a. Similarly, adjacent ends of the second and fourth electrodes 18b and 18d are coupled by another electrical lead 38b. The first pair of electrical leads 38a and 38b thus connect alternately spaced electrodes to form a pair of spaced sensors each comprised of two electrode sections within the combine storage tank 14. When corn is deposited in the storage tank 14, the electrodes are completely covered and encompassed by the corn as shown in FIG. 2 for measuring the electrical conductivity of the corn between spaced, adjacent electrodes as described below.

An opposed end of the third electrode 18c is coupled to a second terminal 62b of the moisture tester 56 by means of the combination of an electrical lead 54a and a second jumper 64b. Similarly, an opposed end of the fourth electrode 18d is coupled to a first terminal 62a of moisture tester 56 by means of the combination of another electrical lead 54b and a first jumper 64a. As shown in the figure, the first terminal 62a is designated "positive" while the second terminal 62b is designated "negative." The second pair of electrical leads 54a, 54b are easily connected and disconnected respectively from the first and second jumpers 64a, 64b by conventional means such as a plug-like or clip-like connector. Each of the jumpers 64a, 64b may be either hard wired or coupled to a respective one of the terminals 62a, 62b in a removable manner. The moisture tester 56 applies a voltage across its first and second terminals 62a, 62b causing a current to flow within each pair of coupled electrodes. The moisture tester 56 then measures the current passing through the corn disposed between adjacent electrodes in the storage tank 14 to determine the moisture content of the corn in terms of its conductivity.

Figure 3:
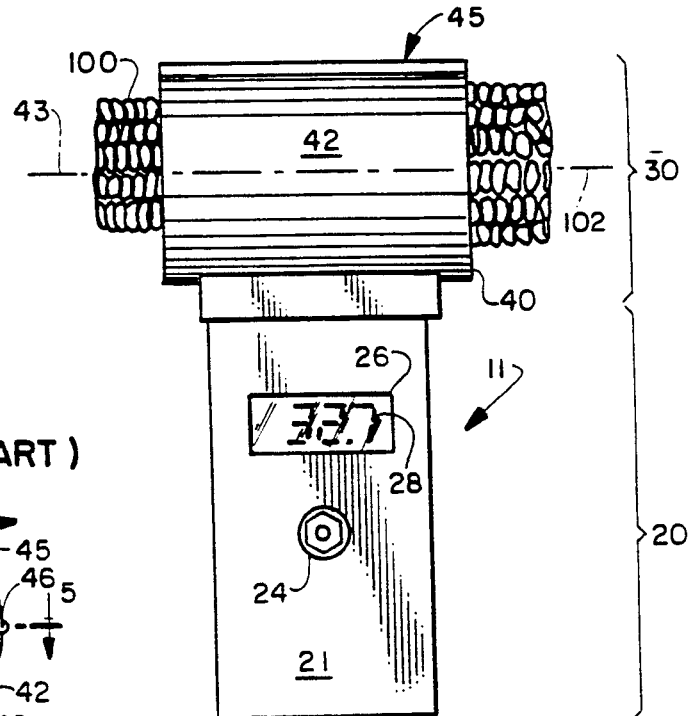
FIG. 3 is a front elevation of a corn moisture tester as used in one embodiment of the present invention, illustrating how an ear of corn (in fragmentary view) is received in the cradle thereof to measure the moisture content of the corn kernels.
Figure 4:
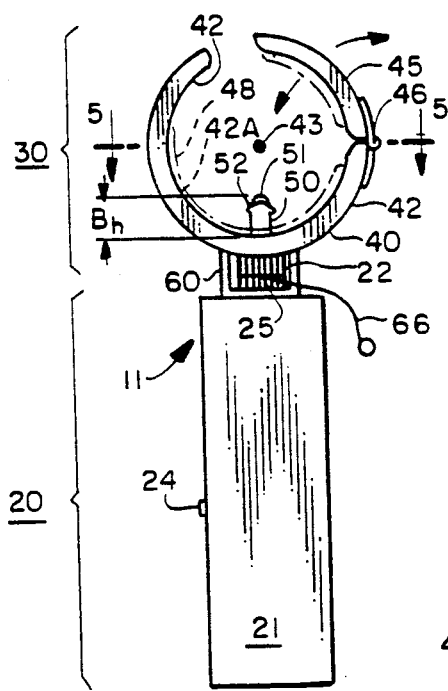
FIG. 4 is a side elevation of the corn moisture tester illustrated in FIG. 3, without the ear of corn.
Figure 5:
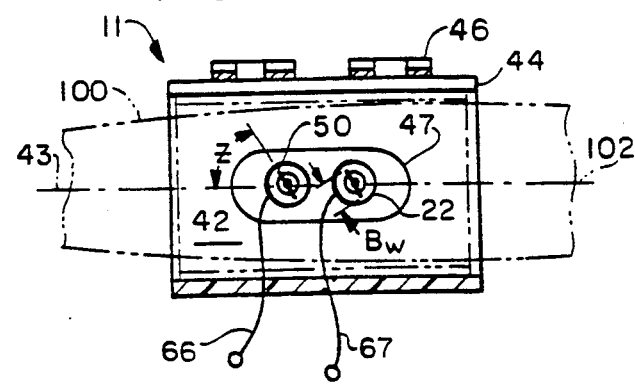
FIG. 5 is a plan view of the corn moisture tester of FIGS. 3 and 4, shown in partial cross-section and having the fragmentary view of the ear of corn illustrated in outline only, to show the configuration and orientation of the conductor blades of the corn moisture tester.

Referring now to FIGS. 3, 4 and 5 there is shown a preferred embodiment of the corn moisture tester for use in the present invention, generally indicated by reference numeral 11. The corn moisture tester 11 is disclosed and claimed in aforementioned U.S. Pat. No. 4,954,783, issued Sep. 4, 1990, to the present inventor, the disclosure of which is incorporated in the present application by reference. The corn moisture tester 11 comprises a moisture meter 20, adapted for measuring the moisture content of corn or other vegetable matter, and a fixture 30 which includes a cradle 40, a pair of conductor blades 50, and a bracket 60 for mounting the cradle 40 to the housing 21 of the meter 20 so that the meter housing also acts as a handle when the moisture tester is removed from a combine for testing the moisture content of kernels on an ear of corn.

The moisture meter 20 may be a commercially available instrument supplied by Delmhorst Instrument Company of Towaco, N.J. The unit 20 is described as a DHM-1 hay moisture meter and functions upon the principal that the electrical resistance of vegetable matter is a function of the moisture content of the vegetable matter. Accordingly, the moisture meter includes an electrical circuit for applying a predetermined voltage between a pair of terminals 22 (FIG. 5). The moisture tester 20 includes a switch 24, mounted to the handle 21, which, when actuated, applies a voltage across the terminals 22. Conductor blades 50 are mounted in the cradle 40 and electrically connected respectively to terminals 22.

Thus, if vegetable matter, such as corn kernels, is placed between and in electrical communication with conductor blades or electrodes 50, the voltage across terminals 22 will cause current to flow therebetween, through the vegetable matter. The magnitude of the current is a measure of the resistance of the vegetable matter, and it gives, when displayed on meter 26, a quantitative measure of the moisture content of the matter. Meter 26 is illustrated in the form of a digital readout which displays a visual indication illustrated at 28 which is calibrated to indicate moisture percentage, rather than current, which the meter actually measures. The signal is, therefore, a useful quantitative representation of the moisture content of the vegetable matter.

While most moisture meters measure electrical resistance between a pair of fixed points, other circuit means may be employed to measure other moisture-dependent properties of corn.

As seen in FIGS. 4 and 5 the electrode blades 50 preferably are flat, thin blades, similar to conventional knife blades used for crafts and hobbies, including a sharp point 51 and knife edges 52 in the form of a chevron when viewed from the side, but honed to a sharp cutting edge. Preferably, the base of each blade 50 (i.e., the portion other than the honed edges) is covered with an electrically non-conducting material or coating so that only the chevron-shaped cutting edge is in electrical contact with the endosperm when the electrodes are embedded in the kernels. Thus, the cutting edges are the only active portions of the electrodes. An alternative electrode construction is an electrode in the form of a needle having a sharpened point providing the active area of the electrode, and the remainder of the needle being coated with an insulating material. The blade shape is preferred over the needle because it insures that at least one row of kernels will be pierced; whereas with a needle, the needle may be placed in an interstice between kernels, requiring replacement before a reading can be taken.

By way of example, for the chevron blade electrode illustrated, the width of the active area may be about one-eighth of an inch, and the base of each electrode is covered with an insulating coating for a distance of at least three-eighths of an inch from the inner surface of the cradle. The electrodes 50 are adapted for piercing the pericarp of a kernel of corn and establishing electrical continuity with the endosperm thereof over a substantial area. The electrodes 50 are fixedly mounted to the terminals 22 of the moisture tester 20 by soldering and the terminals may be mounted to the cradle by suitable insulating potting compound.

The ear cradle 40 includes a fixed cradle section 42 adapted to receive an ear of corn 100 as illustrated in FIGS. 3 and 5. The fixed cradle section 42 is mounted to the handle 21. It has a substantially cylindrical configuration and thereby defines a longitudinal cradle axis 43. When an ear of corn 100 is received in the cradle section 42 the longitudinal axis 102 of the ear of corn 100 and the longitudinal cradle axis 43 are substantially aligned.

The cradle 40 also includes a moveable cradle section or cover 45 mounted to the fixed cradle section 42 by hinge means 46. The hinged cradle cover 45 is opened to permit an ear of corn 100 to be received in the cradle means 40. Thereafter, closing the hinged cradle cover 45 forces the ear of corn 100 onto the piercing electrodes 51 causing each of the electrodes 51 to each pierce at least one of the kernels on the ear of corn 100. The depth of penetration of the conductor blades 50 is limited by the ear of corn 100 abutting the interior surface of the fixed cradle section 42.

Although the hinged cradle cover 45 is not necessary to obtain the desired measurements, it is helpful when holding the handle in one hand, to close the cover 45 with the other hand. This insures that the ear will contact the concave surface 42 of the fixed cradle portion and that, in turn, insures proper penetration depth of the active surfaces of the electrodes.

The cradle 40 which may be fabricated from a section of rigid tubular insulating material is fixedly secured to the moisture meter 20 by mounting bracket 60, in the form of a short, U-shaped section of PVC channel glued to the cradle base 44. The mounting means 60 has holes formed therein. The terminals 22 include a threaded terminal stud (not shown) that is passed through the holes. A threaded terminal cap 25, screwed over the studs, secures the cradle means 40 to the moisture meter 20.

FIG. 5 shows that the terminals 22, and the conductor blades 50 affixed thereto, pass through an opening 47 formed in the cradle base 44. Thus, the conductor blades 50 are in fixed special relation to the interior cradle surface 42.

It is considered important that the configuration and orientation of the conductor blades 50 relative to the interior surface of cradle section 42 and cradle axis 43, insure that each conductor blade will pierce the pericarp and contact the endosperm of at least one kernel of corn, without contacting the cob, when the ear of corn is properly placed in the cradle 42.

FIG. 5 illustrates that the conductor blades 50 each define a blade plane oriented at a predetermined angle Z with respect to the cradle axis 43. Furthermore, the conductor blades 50 define a predetermined blade width $B_w$. FIG. 4 shows that the conductor blades are in fixed relation with the interior cradle surface 42 projecting inwardly a predetermined height $B_h$ above the surface 42.

To prevent the conductor blades 50 from piercing the cob the predetermined blade height $B_h$ should be less than the kernel height $K_h$. For ear corn in the field, kernel moisture may vary widely from ear moisture depending on the state of maturity and the weather.

It should be noted that the configuration and orientation of the conductor blades 50 with respect to the cradle axis 43 insures that when an ear of corn 100 engages the concave inner surface of the fixed cradle section 42, each of the electrodes 50 bridges at least two rows of kernels and straddles at least two adjacent kernels. Thus, each conductor blade 50 penetrates the pericarp and contacts the endosperm of at least one of the kernels on the cob 100. Because the active surfaces of the electrodes 50 project inwardly a predetermined distance from the surface of cradle section 42, the blades 50 penetrate the corn kernels 106 without penetrating the underlying cob. Thus, as the moisture meter 20 applies a constant voltage across terminals 22, only the electrical resistance of the corn kernels, and not the cob nor the husk, is measured.

To insure that each electrode blade 50 bridges at least two rows of kernels and straddles at least two adjacent kernels, the predetermined blade width $B_w$ and predetermined blade angle Z are chosen accordingly. Thus, the component of blade width, $B_w$, which projects in a direction substantially parallel to the cob axis 102, must be greater than the thickness $K_t$ of at least one kernel. Likewise, that component of blade width which projects in a direction substantially normal to the cob axis must be greater than the width of at least one kernel. The plane of each electrode blade 50 forms an angle of approximately 45° with the axis 102 of a corn cob received in the fixed cradle section 42.

FIG. 4 shows that the cradle means 40 may include an optional cradle liner 48 for use when testing the moisture of husked ears. The liner 48 provides a new interior cradle surface 42A which changes the depth of penetration of the blades. The cradle liner or spacer 48 is removable and has a thickness approximately equal to the thickness of the husk on an ear of corn. Thus, moisture tester 11 can be used to measure the moisture of ears that have not been husked when the spacer is removed, and for husked corn when the spacer is inserted.

Also as shown in FIGS. 4 and 5, jumper wires 66 and 67 are coupled to terminals 22 for electrically connecting the corn moisture tester 11 to the previously described bulk corn moisture testing arrangement disposed in the combine's grain storage tank. The jumper wires 66, 67 may be coupled to a respective terminal 22 by conventional means such as soldering. The distal end of each jumper wire 66, 67 is provided with conventional quick disconnect coupling means such as a snap acting or a plug-like connector to facilitate coupling to and decoupling from a respective electrical lead to the array of electrodes in the combine's storage tank as previously described.

Moisture content differences in the total mass of harvested corn are typically measured during corn off-loading. During off-loading the discharge auger is periodically stopped, perhaps as many as five or six times during the emptying of the tank, and moisture readings are taken as the corn passes downward through the electrodes allowing several portions of the entire corn load to be accurately sampled. In this manner, the farmer can obtain a highly accurate reading of the average moisture content of each load of corn recovered by the combine.

There has thus been shown a corn moisture testing arrangement which is adapted for testing the moisture content of corn in bulk form such as in the storage tank of a combine or the moisture content of individual corn kernels on an ear of corn. In a combine, the moisture testing arrangement includes an array of conductive electrodes disposed in a lower portion of the combine storage tank which are electrically coupled to a conventional moisture tester located in the combine's cab. The moisture tester provides a combine operator with a visual indication of corn moisture content which may be used to determine when the corn should be harvested or in providing an estimated dollar value of the corn crop prior to harvesting. The moisture tester is easily disconnected from the electrode array in the combine's storage tank and removed from the combine for testing the moisture content of kernels still on an ear of corn. The inventive corn moisture testing arrangement may thus be used either by a commercial farmer for determining corn moisture content in bulk form, or by corn seed growers for determining drying characteristics of new hybrid seeds under development.

It will be appreciated that while the foregoing description of the corn moisture tester of the invention includes specific details as to elements such as a moisture tester, such details are for the purpose of illustrating the invention and not intended as a limitation of the scope thereof. Persons skilled in the art will be able to modify some of the structure which has been illustrated and to substitute equivalent elements for those disclosed while continuing to practice the principle of the invention; and it is, therefore, intended that all such modifications and substitutions be covered as they are embraced within the spirit and scope of the appended claims.

What is claimed is:

1. In combination with a combine having a storage tank for storing shelled corn, a portable corn moisture tester for measuring the moisture content of corn on the cob including a first pair of kernel-piercing electrodes and an electronic measuring circuit connected to said kernel-piercing electrodes; a second pair of elongated corn-contacting electrodes; insulating means for mounting sad elongated electrodes in mutually spaced relation in a lower portion of the combine storage tank; conductor means connoted to said elongated electrodes in said storage tank and extending externally of said storage tank; and electrical connector means for selectively connecting said electronic measuring circuit to said conductor means, whereby said tester may be used to measure the moisture content of corn on the cob, or the moisture content of shelled corn in said combine storage tank when said electronic measuring circuit is connected to said elongated electrodes by means of said conductor means and said electrical connector means.

2. The corn moisture tester of claim 1, wherein each of said elongated electrodes is comprised of at least one elongated, linear rod-like member.

3. The corn moisture tester of claim 2, wherein each of said rod-like members is comprised of a conductive, phosphor-bronze composition.

4. The corn moisture tester of claim 2 wherein said electrodes include four elongated, linear, rod-like electrodes arranged in a spaced, planar array, and wherein adjacent first ends of alternate spaced electrodes are electrically coupled.

5. The corn moisture tester of claim 4, wherein second ends of two adjacent rod-like electrodes are coupled to said moisture tester.

6. The corn moisture tester of claim 1 wherein said connector means comprises quick disconnect coupling means for electrically connecting said elongated electrodes to said measuring circuit.

7. The corn moisture tester of claim 6, wherein said quick disconnect coupling means includes a plug-in connector.

8. The corn moisture tester of claim 1, wherein the combine further includes a cab and said conductor means extends from said storage tank to said cab.

9. The corn moisture tester of claim 1 further comprising positioning means including a plurality of spaced, non-conductive support members engaging said electrodes and positioned upon a lower portion of the combine storage tank.

10. The corn moisture tester of claim 9, wherein said spaced, non-conductive support members engage a lower portion of the combine storage tank and maintain said electrodes approximately one foot from the bottom of said storage tank.

11. For use in a combine having a grain storage tank incorporating a shelled corn moisture sensing arrangement as well as for use in measuring the moisture content of corn kernels on an ear of corn, a removable moisture tester comprising: a moisture tester for corn having a pair of terminals, meter means for measuring an electrical property of said corn, and visual display means for providing a visual representation of the moisture content of corn; detachable jumper means for electrically coupling the terminals of said moisture tester to the moisture sensing arrangement in the combine's storage tank when said moisture tester is installed in the combine for testing and providing a visual representation of the moisture content of shelled corn; cradle means for receiving and partially enveloping an ear of corn when said moisture tester is not installed in the combine; a pair of electrodes held by said cradle means at a fixed spacing and in electrical communication with said terminals, said electrodes being constructed and arranged such that each electrode pierces the pericarp of at least one of the kernels and is in electrical contact with the endosperm of at least one kernel, without contacting the cob of an ear of corn when said ear of corn is received in said cradle for testing and providing a visual representation of the moisture content of the corn kernels on the ear of corn.

12. The moisture tester of claim 11 further comprising quick disconnect coupling means for coupling said jumper means to the corn moisture sensing arrangement to facilitate installation in and removal of said moisture tester from the combine.

13. The moisture tester of claim 12, wherein said quick disconnect means includes a plug-in connector.

14. The apparatus of claim 11 wherein said cradle means includes a cover and a fixed section having a generally semi-cylindrical shape adapted to fit about an ear of corn received therein for a major portion of the periphery of said ear and wherein said fixed section and said cover cooperate to substantially encompass an ear when said cover is moved to a closed position.

15. The apparatus of claim 11 wherein said electrodes are blades having a height less than the height of a kernel of corn intended to be measured, and a width at least as great as the width of a kernel of corn intended to be measured as it is seated on an ear and a thickness substantially less than either the height or the width.

16. The apparatus of claim 15 wherein each of said blades defines a surface plane, the surface planes of said conductor blades being substantially parallel to one another and each defining an acute angle with the axis of a corn cob received in said fixed cradle section.

17. The apparatus of claim 16 wherein said acute angle is approximately 45°.

18. Apparatus for measuring the moisture content of shelled corn in bulk form deposited in a storage tank of a combine or of at least one kernel on an ear of corn, said apparatus comprising:
a first pair of electrodes disposed in the combine storage tank;
a moisture tester for corn having a pair of terminals, meter means for measuring an electrical property of said corn, and visual display means for presenting a visual indication of said electrical property;
jumper means for coupling the terminals of said moisture tester to said first pair of electrodes in the combine storage tank whereupon said moisture tester measures and displays said electrical property for shelled corn in bulk form in the combine storage tank, said jumper means including means for facilitating decoupling from said first pair of electrodes;
cradle means attached to said moisture tester for receiving and partially enveloping an ear of corn; and
a second pair of electrodes held by said cradle means at a fixed spacing and in electrical communication with said terminals, said second pair of electrodes being constructed and arranged such that each of said second electrodes pierces a peripcarp and is in electrical contact with an endosperm of said at least one kernel, without contacting a cob to which said at least one kernel is attached when an ear of corn is received in said cradle and said jumper means is decoupled from said first pair of electrodes for measuring the moisture content of said at least one kernel on an ear of corn.

* * * * *

UNITED STATES PATENT AND TRADEMARK OFFICE
CERTIFICATE OF CORRECTION

PATENT NO. : 5,126,679
DATED : June 30, 1992
INVENTOR(S) : Robert H. Spry

It is certified that error appears in the above-identified patent and that said Letters Patent is hereby corrected as shown below:

Col. 4, line 16, "gauge" should be --auger--.

Claim 1, Col. 8, line 28, "sad" should be --said--, and line 30, "connoted" should be --connected--.

Signed and Sealed this

Seventeenth Day of August, 1993

Attest:

BRUCE LEHMAN

*Attesting Officer*      *Commissioner of Patents and Trademarks*